(12) United States Patent
Chen

(10) Patent No.: US 6,437,038 B1
(45) Date of Patent: Aug. 20, 2002

(54) PRESSURE SENSITIVE ADHESIVE COMPOSITION

(75) Inventor: Fei Chen, Lynge (DK)

(73) Assignee: Coloplast, Humlebaek (DK)

( * ) Notice: Subject to any disclaimer, the term of this patent is extended or adjusted under 35 U.S.C. 154(b) by 0 days.

(21) Appl. No.: 09/599,638

(22) Filed: Jun. 23, 2000

Related U.S. Application Data

(63) Continuation-in-part of application No. 09/265,563, filed on Mar. 9, 1999, now abandoned, which is a continuation-in-part of application No. 09/053,052, filed on Apr. 1, 1998, now abandoned.

(30) Foreign Application Priority Data

Mar. 12, 1998 (DK) ............................................... 0360/98

(51) Int. Cl.$^7$ .............................. C08J 3/00; C08K 3/20; C08K 5/01; C08L 15/00; A61F 13/02

(52) U.S. Cl. ....................... 524/474; 523/111; 524/22; 524/23; 524/28; 524/31; 524/55; 524/490; 524/491; 424/448; 602/41; 602/52; 602/56; 604/307

(58) Field of Search ............................... 524/22, 23, 28, 524/31, 55, 474, 490, 491; 523/111; 604/307; 602/41, 52, 56; 424/448

(56) References Cited

U.S. PATENT DOCUMENTS

| | | |
|---|---|---|
| 2,339,549 A | 1/1944 | Morse |
| 4,192,785 A | 3/1980 | Chen et al. |
| 4,204,540 A | 5/1980 | Cilento |
| 4,231,369 A | 11/1980 | Sorensen et al. |
| 4,367,732 A | 1/1983 | Poulsen et al. |
| 4,427,737 A | 1/1984 | Cilento et al. |
| 4,477,325 A | 10/1984 | Osburn |
| 4,496,357 A | 1/1985 | Osburn |
| 4,551,490 A | 11/1985 | Doyle et al. |
| 4,952,618 A | 8/1990 | Olsen |
| 5,006,401 A | 4/1991 | Frank |
| 5,633,010 A | 5/1997 | Chen |

FOREIGN PATENT DOCUMENTS

| | | |
|---|---|---|
| EP | 0 081 907 | 5/1986 |
| EP | 0 122 344 | 7/1987 |
| EP | 0 272 149 | 6/1988 |
| EP | 0 340 945 | 11/1993 |
| FR | 2 733 508 | 10/1996 |

*Primary Examiner*—Patrick D. Niland
(74) *Attorney, Agent, or Firm*—Jacobson Holman, PLLC

(57) ABSTRACT

A pressure sensitive adhesive composition suitable for medical purposes comprising a rubbery elastomeric base and one or more water soluble or water swellable hydrocolloids, the adhesive composition comprising a substantially homogeneous mixture of 15–60% of a butyl rubber, 15–60% of one or more tackifier resins, 1–10% of a tackifying liquid constituent, 20–60% of one or more hydrocolloids and 0–3% of a pigment shows very good properties as an adhesive for ostomy appliances.

9 Claims, 1 Drawing Sheet

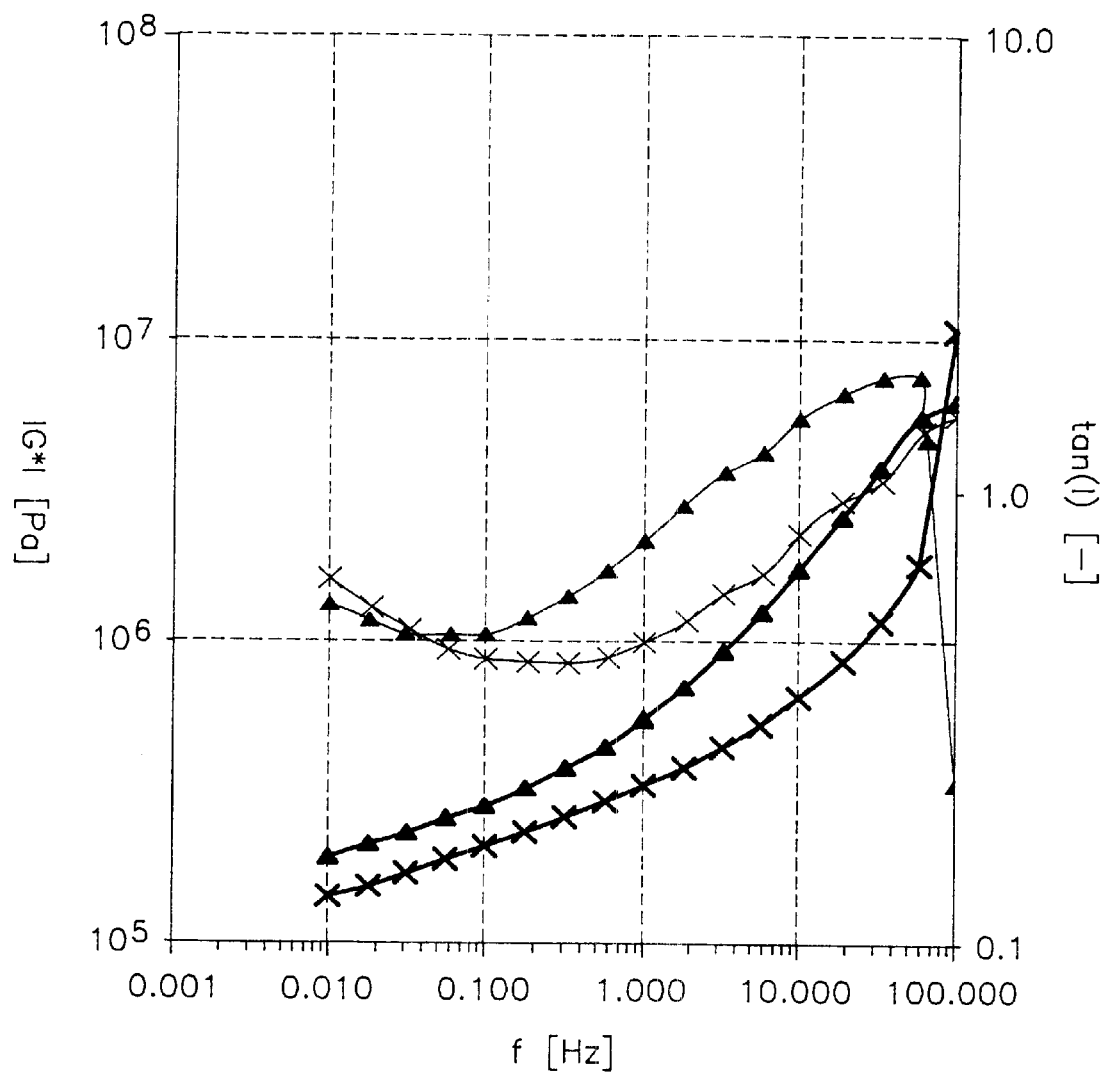

PRESSURE SENSITIVE ADHESIVE COMPOSITION

This is a continuation-in-part of U.S. Ser. No. 09/265,563, filed Mar. 9, 1999 now abandoned, which in turn is a continuation-in-part of U.S. Ser. No. 09/053,052, filed Apr. 1, 1998, now abandoned.

BACKGROUND OF THE INVENTION

1. Field of the Invention

The present invention relates to pressure sensitive adhesive compositions suitable for various medical applications and especially suitable for use for adhesion to the skin, in particular in the field of ostomy care. More specifically, this invention relates to adhesive compositions comprising a rubbery elastomeric base and one or more water soluble or water swellable hydrocolloids dispersed therein, the use of such adhesive compositions for the preparation of a wound dressing or an adhesive wafer for an ostomy appliance, and to wound dressings or ostomy appliances comprising such adhesive composition.

In connection with surgery for a number of diseases in the gastro-intestinal tract a consequence is, in many cases, that the colon, the ileum or the urethra has been exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula, the patient will have to rely on an appliance to collect the bodily material emerging from such opening.

2. Description of the Related Art

Various skin adhesive agents are used today for the above mentioned purposes.

Such adhesives should have a composition which is sufficiently tacky to secure the appliance or skin barrier to the abdomen, and a cohesion ensuring safe removal thereof without leaving residues on the skin. Furthermore, the adhesive should show a degree of elasticity to enable the adhesive layer of the appliance or barrier to follow the movements of the patient without slipping the skin and should also show a great resistance to erosion caused by aggressive exudates from an ostomy in order to minimise the risk of leakage.

A very widespread embodiment of skin adhesive agents comprises a self-adhesive elastomeric matrix, in which water-absorbing, swelling particles, the so-called hydrocolloids, are dispersed.

Adhesive compositions comprising hydrocolloids have been known for many years. U.S. Pat. No. 3,339,549 discloses a blend of a rubbery elastomer such as polyisobutylene and one or more water soluble or water swellable hydrocol-loids such as a powdery mixture of pectin, gelatine and carboxymethylcellulose. The adhesive mass has a water-insoluble film applied to one surface. A composition of this type is available commercially from E.R. Squibb & Sons Inc. under the trademark "Stomahesive" and is used as a skin barrier around stomas to prevent skin breakdown by the corrosive fluids discharged by the stoma.

In adhesive compositions of this type, the polyisobutylene is responsible for provision of the adhesive properties and the dispersed hydrocolloid powders absorb fluid and render the adhesive agent capable of also adhering to moist skin (wet tack). These compositions are also gaining increasing acceptance as wound dressings for dermal ulcers, burns and other exuding wounds. One major problem which has been encountered with conventional adhesive compositions comprising hydrocolloids is their susceptibility to breakdown upon exposure to body fluids. When the compositions are used as skin barriers, e.g., around stomas, absorption of fluid is desirable, but excessive swelling causes the composition to lose its integrity opening for leaks and the barrier must be replaced more often than is desirable from a skin protection point of view, and very often, a residue remains on the skin, which in many cases is difficulty to remove.

A number of attempts have been made to improve the properties of adhesive compositions in order to overcome the above-mentioned drawbacks.

U.S. Pat. Nos. 4,192,785 and 4,551,490 describe incorporating into an adhesive composition of a cohesive strengthening agent such as a natural or synthetic fibrous material, finely divided cellulose, cross-linked dextran, cross-linked carboxymethylcellulose or a starch-acrylonitrile graft copolymer. The cohesive strengthening agent is stated to control the rate of hydration of the composition thereby increasing the resistance against breakdown by body fluids.

U.S. Pat. No. 4,477,325 describes incorporation of a mixture of a copolymer resin of ethylene and vinyl acetate (EVA) into the adhesive composition. After mixing and moulding, the composition is subjected to ionising radiation to form a cross-linked polymer network of the EVA or comprising EVA and another cross-linked resin. The cross-linked matrix is said to provide a controlled swelling.

U.S. Pat. No. 4,496,357 describes the incorporation of fumed silica into adhesive compositions to control swelling.

EP Patent No. 0 122 344 B1 describes incorporation of one or more natural or synthetic polymers capable of developing elastomeric properties when hydrated, such as gluten and long chain polymers of methyl vinyl ether/maleic acid, into the adhesive composition. The adhesive composition is stated to be resistant to erosion by moisture and body fluids.

EP Patent No. 0 340 945 B1 describes incorporation of some polycationic hydrocolloid particles into a hydrocolloid composition. The mixture of polycationic, polyanionic and neutral hydrocolloids is stated to provide increased integrity without a concomitant decrease in absorbing capacity.

In other embodiments, styrene copolymers have been incorporated which is disclosed in a number of patent references.

In U.S. Pat. No. 4,231,369, Sorensen et al. disclose an ostomy skin barrier consisting of a physically cross-linked styrene copolymer having dispersed therein a water soluble hydrocolloid gum, a tackifier and optionally an oil extender.

In U.S. Pat. No. 4,367,732, Poulsen et al. disclose an ostomy skin barrier consisting of a water soluble hydrocolloid dispersed in a continuous phase consisting of a physically cross-linked elastomer, a hydrocarbon tackifier, and a plasticizer, an antioxidant, and optionally an oily extender.

U.S. Pat. No. 4,427,737 (Cilento et al.) discloses a breathable tape having a porous backing and a microporous adhesive layer comprising from about 30% to about 60% by weight rubbery elastomer selected from the group consisting of natural rubber, polyurethane rubber, and polyisobutylene, from 20% to about 65% by weight of one or more water soluble or water swellable hydrocolloids and up to 35% by weight of one or more tackifiers, plasticizers, antioxidants and preservatives.

In U.S. Pat. No. 5,633,010, Chen discloses a hydrocolloid composition comprising a unsaturated aliphatic homopolymer (20–50%) cross-linked by gamma radiation, a compatible tackifier (20–60%) and at least one hydrocolloid absorbent (5–60%).

U.S. Pat. No. 5,006,401 (Frank) discloses a composite compression dressing comprising 5–30% by weight of one or more polyisobutylenes or a blend of one or more polyisobutylenes and butyl rubber, from 3 to 30% by weight of one or more styrene radial or block copolymers, from 8 to about 40% by weight mineral oil and from 15 to 65% by weight of one or more water soluble hydrocolloid gums and up to 15% by weight of one or more water swellable cohesive strengthening agents, from 7.5 to 15% by weight of a tackifier and up to about 5% by weight of optional ingredients.

U.S. Pat. No. 4,551,490 (Doyle et al.) discloses medical grade pressure sensitive adhesive compositions comprising a homogeneous mixture of 5–30% of one or more polyisobutylenes, 3–20% of one or more styrene radial or block type copolymers, mineral oil, one or more water soluble hydrocolloid gums, and a tackifier. One or more water swellable cohesive strengthening agents, an antioxidant, and various other optional ingredients also may be included within the adhesive composition.

EP Patent publication No. 81907 discloses an ostomy appliance comprising a skin barrier (A) surrounding the stoma and a coupling element (B) including an outwardly extending flange permanently affixed to the skin barrier (A) and a microporous adhesive layer (C) having an upper porous layer. The skin barrier adhesive (A) comprises a homogeneous 30–70% of a blend of low molecular weight polyisobutylene and one or more optional thermoplastic elastomers selected from medium molecular weight polyisobutylene, butyl rubber, and styrene isoprene copolymers and having dispersed therein 35–65% of one or more water soluble hydrocolloids and one or more water swellable or inert cohesive strengthening agents.

Generally speaking, these prior methods are superior to improve the integrity of adhesive compositions. Nevertheless, need still exists for better adhesive composition having resistance to biological fluids as well as the properties of improved adhesion to the skin and strechability.

Now it has been found that an improved adhesive composition having resistance to biological fluids as well as the properties of improved adhesion to the skin and strechability may be obtained.

SUMMARY OF THE INVENTION

The present invention relates to a pressure sensitive adhesive composition suitable for various medical applications and especially suitable for use for adhesion to the skin, in particular in the field of ostomy care. More specifically, this invention relates to adhesive compositions comprising a rubbery elastomeric base and one or more water soluble or water swellable hydrocolloids dispersed therein, ostomy appliances comprising such adhesive compositions and the use of such adhesive compositions for preparing wound dressings or ostomy appliances.

BRIEF DESCRIPTION OF THE DRAWINGS

The invention is explained more in detail with reference to the drawings in which FIG. 1 is a diagram showing loss tangent (tan δ) curve and the complex shear modulus G*[Pa] of two compositions according to the invention.

DETAILED DESCRIPTION OF THE PRESENT INVENTION

The present invention relates to a pressure sensitive adhesive composition suitable for medical purposes comprising a rubbery elastomeric base and one or more water soluble or water swellable hydrocolloids, said adhesive composition comprising a substantially homogeneous mixture of 15–60% of a butyl rubber, 15–60% of one or more tackifier resins, 1–10% of a tackifying liquid constituent, 20–60% of one or more hydrocolloids and 0–3% pigment.

The pressure sensitive adhesive compositions of the present invention differ from the compositions disclosed in U.S. Pat. Nos. 4,231,369 4,427,737 and, 5,633,010 in that they comprise 15–60% butyl rubber and in that the compositions of the invention comprise 1–10% of a tackifying liquid.

The pressure sensitive compositions of the invention differs from the compositions disclosed in U.S. Pat. No. 5,006,401 in that they comprise 1–10% of a tackifying liquid and in that the tackifying resin is present in an amount above 15%.

The pressure sensitive adhesive compositions of the present invention differ from the compositions disclosed in U.S. Pat. No. 4,367,732 in that they comprise butyl rubber and no physically cross-linked elastomer or polar plasticizer therefor.

The adhesive compositions according to the invention show a very strong erosion resistance, and the new adhesive provide a significantly longer wear-time for those patients using appliances with the adhesive compositions of the invention.

Without limiting the invention to any hypothesis it is believed that the combination of the rubbery elastomer, one or more tackifier resins and a tackifying liquid constituent in the proportions stated above provides extensibility and both rapid and complete recovery from modular strains to the composition. The combination of the adhesive properties of the rubbery elastomer and one or more tackifier resins and tackifying liquid constituent and the absorbing properties of the hydrocolloids renders the adhesive composition of the invention especially suitable for use in ostomy appliances.

The contents of butyl rubber in the compositions according to the invention is preferably from 15 to 45% and more preferably from 20 to 35%. The contents of tackifier resin is preferably 15 to 45% and more preferably from 20 to 35%. The amount of tackifying liquid in the compositions of the invention is suitably from 2 to 9%, more preferably from 3 to 7% and especially about 5%.

In a preferred embodiment, the adhesive comprises a substantially homogeneous mixture of 20–30% of butyl rubber, 20–30% of one or more tackifier resins, 3–7%, preferably at least 5%, of a tackifying liquid constituent, and 30–55% of one or more hydrocolloids The rubbery component is preferably a non-staining, medium unsaturated isoprene-isobutylene copolymer having a Mooney viscosity about 50 pts when determined according to ISO-289.

The tackifying resin is preferably a hydrocarbon tackifier resin and is more preferably selected from the group comprising polymers and copolymers of cyclopentadiene, dicyclopentadiene, alpha-pinene or beta-pinene.

The tackifying liquid constituent is suitably a liquid paraffin.

Suitable hydrocolloids for incorporation in the adhesive compositions of the invention are selected from naturally occurring hydrocolloids, semisynthetic hydrocolloids and synthetic hydrocolloids.

More particularly, the hydrocolloids are preferably selected from guar gum, locust bean gum (LBG), pectin, alginates, gelatine, xanthan and/or gum karaya; cellulose derivatives (e.g. salts of carboxymethylcellulose such as sodium carboxymethylcellulose, methylcellulose and hydroxypropylmethylcellulose) and/or sodium starch glycolate and/or polyvinylalcohol and/or polyethylene glycol.

It is preferred to use a combination of two or more hydrocolloids. It is especially preferred to use a combination of pectin, gelatine and carboxymethylcellulose as the hydrocolloid component.

The total amount of hydrocolloids is preferably 40–50% of the total composition.

An especially preferred composition according to the invention comprises 25% of butyl rubber, 25% of tackifying resin, 5% of tackifying oil and 45% of a mixture of hydrocolloids comprising gelatine, pectin and CMC.

The pigment optionally being present in the compositions according to the invention may be any pharmaceutically acceptable pigment such as zinc oxide or titanium dioxide.

In a further aspect, the invention relates to the use of an adhesive composition comprising a rubbery elastomeric base and one or more water soluble or water swellable hydrocolloids, said adhesive composition comprising a substantially homogeneous mixture of 15–60% of a butyl rubber, 15–60% of one or more tackifier resins, 1–10% of a tackifying liquid constituent, and 20–60% of one or more hydrocolloids for securing ostomy appliances to the skin and for sealing around an ostomy, for securing wound dressings or wound drainage bandages to the skin, for securing devices for collecting urine to the skin, or for securing orthoses or prostheses to the skin.

In a still further aspect, the invention relates to an ostomy appliance for placing on the abdomen of a patient for use in collecting discharge of visceral contents comprising an adhesive composition containing a substantially homogeneous mixture of 15–60% of a butyl rubber, 15–60% of one or more tackifier resins, 1–10% of a tackifying liquid constituent, and 20–60% of one or more hydrocolloids.

An ostomy appliance according to the invention may be an open or a closed appliance suitable for use in connection with a colostomy, an ileostomy or a urostomy. It may be a one-piece appliance or a body side member or face plate forming part of a two-piece appliance comprising the body side ostomy member and a separate collection bag and optionally comprising a convex member. A separate collection bag may be attached to the body side member in any convenient manner known per se, e.g. via a coupling ring or by a flange covered with an adhesive.

An ostomy appliance according to the invention may be made from materials conventionally used for the preparation of ostomy appliances in a manner known per se in the field. In a preferred embodiment of an ostomy appliance of the invention, the adhesive plate for securing the appliance to the abdomen of the user is of the kind comprising two different adhesives in a roll of the kind disclosed in WO 89/05619.

In a yet further aspect, the invention relates to a method of securing an ostomy appliance to skin and for sealing around an ostomy, for securing a wound dressing or wound drainage bandage to the skin, for securing a device for collecting urine to skin comprising applying to the skin an adhesive composition of the invention.

All percentages stated in this specification are by weight unless otherwise stated.

The invention is illustrated more in detail in the below Examples disclosing embodiments of the invention.

MATERIALS AND METHODS

Butyl Rubber: Polysar Butyl 101-3 from Bayer AG

Paraffin oil: PL-500 from Rode & Rode A/S

Arkon P-90 from Arakawa Forest Chemical Industries Ltd. A hydrogenated cyclopentadiene tackifier.

Gelatine: Gelatine P.S.98.240.233 available from ED. Geistlich Sohne AG.

Pectin: Pectin LM 12CG Z or Pectin USP/100 from Copenhagen Pectin A/S. CMC: Sodium carboxymethylcellulose available from Akzo under the tradename Akucell® AF2881

A Z mixer Type LKB 025 from Herman-Linden was used.

EXPERIMENTAL PART

EXAMPLE 1

Preparation of an adhesive material according to the invention having the composition stated in the below Table 1:

TABLE 1

| Ingredient | Percent by weight |
|---|---|
| Butyl rubber | 25 |
| Arkon P-90 | 20 |
| Paraffin oil | 5 |
| Gelatine | 20 |
| Pectin | 20 |
| CMC | 10 |

100 grams of butyl rubber was added in to Z-mixer at 160° C. and softened for about 5 minutes. Then 80 grams of Arkon P-90 and 20 grams of paraffin oil were added and mixing was continued at 160° C. and 50 mbar until the blend was homogeneous. The mass was cooled to 80° C., and 100 grams of the mass was removed from the mixer. To the remained mass was added 40 grams of gelatine, 40 grams of pectin and 20 grams of CMC. Mixing is continued under 80° C. and 50 mbar until a homogeneous dough was formed.

While still hot and soft, the resulting dough-like mass was then removed from the mixer and formed into sheet stock material having a thickness of approximately 1 mm by compression moulding the adhesive mass at approximately 90° C. and 100 Bar between two sheets of silicone release paper. The resultant flat plate was then cut into pieces having the desired shapes.

The adhesive composition may be used for securing ostomy appliances to the skin and for sealing around an ostomy, for securing wound dressings or wound drainage bandages to the skin, for securing devices for collecting urine to the skin, or for securing orthoses or prostheses to the skin. The ostomy appliances or wound dressings may be any such product known per se and may be prepared in a manner analogous to the preparation of similar products using conventional adhesive compositions.

EXAMPLES 2–8

Following the procedure disclosed in Example 1 adhesive compositions according to the invention having the compositions stated in the below Table 2 were prepared.

TABLE 2

| Ingredient | Example 2 | Example 3 | Example 4 | Example 5 |
|---|---|---|---|---|
| Butyl rubber | 25 | 25 | 20 | 25 |
| Arkon P-90 | 25 | 25 | 25 | 22.5 |
| Paraffin oil | 5 | 8.5 | 5 | 8.5 |
| Gelatine | 20 | 18.25 | 20 | 19.5 |
| Pectin | 20 | 18.25 | 25 | 19.5 |
| CMC | 5 | 5 | 5 | 5 |

| Chemicals | Example 6 | Example 7 | Example 8 |
|---|---|---|---|
| Butyl rubber | 25 | 25 | 20 |
| Arkon P-90 | 25 | 20 | 20 |
| Paraffin oil | 5 | 10 | 5 |
| Gelatine | 19.85 | 20 | 22.5 |
| Pectin | 20 | 20 | 22.5 |
| CMC | 5 | 5 | 10 |
| Titanium dioxide | 0.15 | | |

EXAMPLE 9

Test of ostomy appliances having an adhesive plate according to the invention as compared to a commercially available ostomy appliance.

A trial has been carried out in which 50 evaluable patients participated in the test, 29 ileostomates and 21 urostomates.

The trial was carried out as a comparative, crossover test with two test products—an existing commercial product available under the trademark Assura collection with adhesive for long wear-time (with zinc oxide) and a corresponding a collection bag having an adhesive plate comprising the adhesive according to Example 2.

The test results showed that the new adhesive based on butyl rubber performs significantly better regarding the parameter "the feeling of security" compared to Assura adhesive for long wear-time (with zinc oxide). Furthermore, the adhesive showed excellent properties with respect to adhesion and absorbing properties.

Thus, the adhesive according to the invention showed stronger erosion resistance, and the new adhesive provided a significantly longer wear-time for those patients using these appliances, 95 hours compared to the 70 hours by the Assura appliance with adhesive for long wear-time (with zinc oxide) ($p<0.001$) as appears from the below Table 3.

TABLE 3

Wear Time in Hours for Ostomy Appliance According to the invention as Compared With Assura adhesive for long wear-time (with zinc oxide).

| | # Test persons | Mean | Median | Minimum | Maximum | Std Deviation |
|---|---|---|---|---|---|---|
| Invention | 50 | 94.73 | 92.00 | 22.00 | 174.00 | 36.58 |
| Assura Wear-Life | 50 | 69.55 | 71.75 | 18.63 | 113.75 | 17.77 |

EXAMPLE 10

Comparison of water absorption and gel strength for the compositions of Examples 2 (Sample 1) and 7 (sample 2) of the present invention, and a state of the art adhesive (sample 3) comprising polyisobutylene and butyl rubber in admixture with 10% tackifier resin and hydrocolloids.

Water Absorption Measurement

The adhesive was pressed into a plate with a thickness of 1 mm. A sample of 25×25 mm was then punched out and adhered on an object glass (slide). The object glass with the sample was weighed and placed in a beaker with 0,9% isotonic saline at 37° C. After 2 hours, the object glass with the sample was removed from the beaker, the water was shaken off, and the object glass with the sample was weighed again after drying the surface of the object glass not covered with adhesive. The increase of weight was recorded as the water absorption.

Gel Strength Measurement

The adhesive was pressed into a plate with a thickness of 1 mm. A sample with an diameter of 50 mm was punched out and adhered on a 80 mm Petri dish. 0,9% isotonic saline was poured into the Petri dish until the sample is totally covered. A lid was put on. After 18 hours, the samples were evaluated for their gel strength according to an internal system using five reference adhesives having different gel strengths.

| Sample no. | Water absorption | Gel strength |
|---|---|---|
| 1 | 0.086 $g/cm^2/2$-hrs | 5 |
| 2 | 0.089 $g/cm^2/2$-hrs | 4 |
| 3 | 0.216 $g/cm^2/2$-hrs | 3 |

Sample 1 and 2 showed the same level of water absorption which was much lower than that of sample 3.

Sample 1 had the highest gel strength, and sample 3 had the lowest. The gel strength decreases with increasing number for sample 1 to 3.

Samples 1 and 2 show a combination of a low water absorption and high gel strength rendering them very erosion resistant in contrast to samples 3 having high water absorption and low gel strength. From these results it may be expected that the adhesives of the invention will provide a longer wear time than sample 3. This has been confirmed by a clinical trial where in an adhesive made of sample 1 provided a significantly longer wear time than the adhesive of sample 3.

EXAMPLE 11

Test of the elastic properties as measured by Dynamic Mechanical Analysis of the compositions of Examples 2 (Sample 1) and 7 (sample 2) of the present application has been carried out.

DMA (Dynamic Mechanical Analysis) Test

A DMA analysis was carried out for sample 1 and 2. The analysis was carried out by using a Haake RS150 apparatus with a sensor of 8 mm plate /plate. A frequency sweep was run for samples 1 and 2 at a temperature of 32° C.

Samples 1 and 2 had similar formulations, the difference being that the contents of paraffin oil is 10% in sample 2, and 5% in sample 1, and the contents of tackifier resin is 20% in sample 2 and 25% in sample 1.

The result is presented on the diagram shown in FIG. 1.

The curves with triangle symbols (▲) are for sample 1, and the curves with cross symbols (x) are for sample 2.

The upper, green set of curves are representing the tan δ. The lower loss tangent (tan δ) curve for sample 2 demonstrates that due to the 5% increase of paraffin oil, sample 2 becomes much more plastic as compared to sample 1.

The lower, blue set of curves represent the complex shear modulus G*[Pa]. The curve for the complex shear modulus G*[Pa] for sample 2 is essentially parallel to and shifted downwards as compared to that of sample 1. This means that sample 2 is less resistant when exposed to a mechanical stress than sample 1.

Based on the DMA study it is indicated that the amount of paraffin oil is a critical parameter for this kind of adhesive system. In order to ensure a superior erosion resistance combined with high resistance to mechanical stress, it is recommended that formulation for the adhesive system described in this patent should not contain more than about 10% paraffin oil in order to con serve a sufficient resistance to mechanical stresses. This is essential in order to provide an adhesive having a sufficient cohesion to ensure that it may easily be removed from the skin without leaving residues on the skin.

What is claimed is:

1. A pressure sensitive adhesive composition suitable for medical purposes and which comprises a rubbery elastomeric base in which a water soluble or water swellable hydrocolloid, a combination of pectin, gelatine and carboxymethylcellulose, is substantially homogeneously dispersed, said adhesive composition comprising, as sole essential components, an admixture of from 15 to 60 percent by weight of butyl rubber, from 15 to 60 percent by weight of tackifier resin, from 1 to 10 percent by weight of tackifying liquid constituent, from 20 to 60 percent by weight of hydrocolloid and, optionally, up to 3 percent by weight of pigment.

2. An adhesive composition as claimed in claim 1 wherein the butyl rubber is a non-staining, medium unsaturated isoprene-isobutylene copolymer having a Mooney viscosity about 50 pts when determined according to ISO-289.

3. An adhesive composition as claimed in claim 1 wherein the tackifying resin is a hydrocarbon tackifier resin.

4. An adhesive composition as claimed in claim 3 wherein the hydrocarbon tackifier resin is a polymer or copolymer of cyclopentadiene, dicyclopentadiene, alpha-pinene or beta-pinene.

5. An adhesive composition as claimed in claim 1 wherein the tackifying liquid constituent is a liquid paraffin.

6. An adhesive composition as claimed in claim 1 wherein the hydrocolloids are naturally occurring hydrocolloids, semisynthetic hydrocolloids or synthetic hydrocolloids.

7. An adhesive composition as claimed in claim 6 wherein the hydrocolloids are guar gum, locust bean gum (LBG), pectin, alginates, gelatine, xanthan or gum karaya or combinations thereof; cellulose derivatives, sodium starch glycolate, polyvinylalcohol or polyethylene glycol, or combinations thereof.

8. An ostomy appliance for placing on the abdomen of a patient for use in collecting discharge of visceral contents which comprises an adhesive composition as claimed in claim 1.

9. A method of securing an ostomy appliance to skin and for sealing around an ostomy, for securing a wound dressing or wound drainage bandage to skin, or for securing a device for collecting urine to skin, which method comprises applying to the skin an adhesive composition as claimed in claim 1.

* * * * *